United States Patent [19]

Mueller et al.

[11] Patent Number: 5,300,036
[45] Date of Patent: Apr. 5, 1994

[54] TROCAR WITH MULTIPLE CONVERTERS AND DETACHABLE OBTURATOR

[75] Inventors: Richard L. Mueller, Byron; Edwin J. Hlavka, Palo Alto; Tim Kovac, Los Gatos; Albert K. Chin, Palo Alto, all of Calif.

[73] Assignee: Origin Medsystems, Inc., Menlo Park, Calif.

[21] Appl. No.: 41,914

[22] Filed: Apr. 2, 1993

Related U.S. Application Data

[63] Continuation of Ser. No. 753,326, Aug. 30, 1991, abandoned.

[51] Int. Cl.⁵ .............................................. A61M 5/178
[52] U.S. Cl. ..................................... 604/167; 604/164; 604/264
[58] Field of Search ............... 604/164, 165, 167, 169, 604/256, 264; 137/843, 846, 847, 849, 850, 852; 606/185

[56] References Cited

U.S. PATENT DOCUMENTS

| | | |
|---|---|---|
| 3,994,287 | 11/1976 | Turp et al. |
| 4,601,710 | 7/1986 | Moll .................................. 604/165 |
| 4,654,030 | 3/1987 | Moll et al. .......................... 604/165 |
| 4,723,550 | 2/1988 | Bales et al. ......................... 604/256 |
| 4,931,042 | 6/1990 | Holmes et al. ..................... 604/117 |
| 4,932,633 | 6/1990 | Johnson et al. .................... 604/256 |
| 5,030,206 | 7/1991 | Lander ............................... 604/164 |
| 5,053,016 | 10/1991 | Lander ............................... 604/169 |
| 5,114,407 | 5/1992 | Burbank ............................. 604/164 |
| 5,116,353 | 5/1992 | Green ................................. 606/184 |
| 5,127,909 | 7/1992 | Shichman ........................... 604/165 |

FOREIGN PATENT DOCUMENTS

| | | |
|---|---|---|
| 0051718 | 8/1981 | European Pat. Off. |
| 0113520 | 7/1984 | European Pat. Off. |
| 0413493A3 | 8/1990 | European Pat. Off. |
| 0424002A1 | 4/1991 | European Pat. Off. |
| 2284303 | 9/1975 | France. |

OTHER PUBLICATIONS

Sakata, et al.; "Usefulness of a Preoperative Indwelling Endoscopic Nasobiliary Drainage Tube and Intraoperative CUSA in Laparoscopic Cholecystectomy"; *Surgical Laparoscopy & Endoscopy*, vol. 1, No. 2, 1991, at p. 130.

United States Surgical Corporation; copy of a 1991 catalog page showing a removable converter produced by this company.

*Primary Examiner*—John J. Wilson
*Attorney, Agent, or Firm*—Limbach & Limbach

[57] ABSTRACT

An improved trocar is provided which includes converters for adapting to different size surgical instruments while maintaining sealing. The invention also includes an improved trocar tube body seal design which accepts and accommodates surgical tool angulation while still maintaining sealing. Still further, the invention provides a trocar obturator with a snap-fit joint which permits the forward portion of the obturator to be detached from the trocar body and separately used with the trocar tube subassembly. With this option, a latch mechanism is configured opposite to a converter to retain the obturator fixed with the trocar tube subassembly.

29 Claims, 4 Drawing Sheets

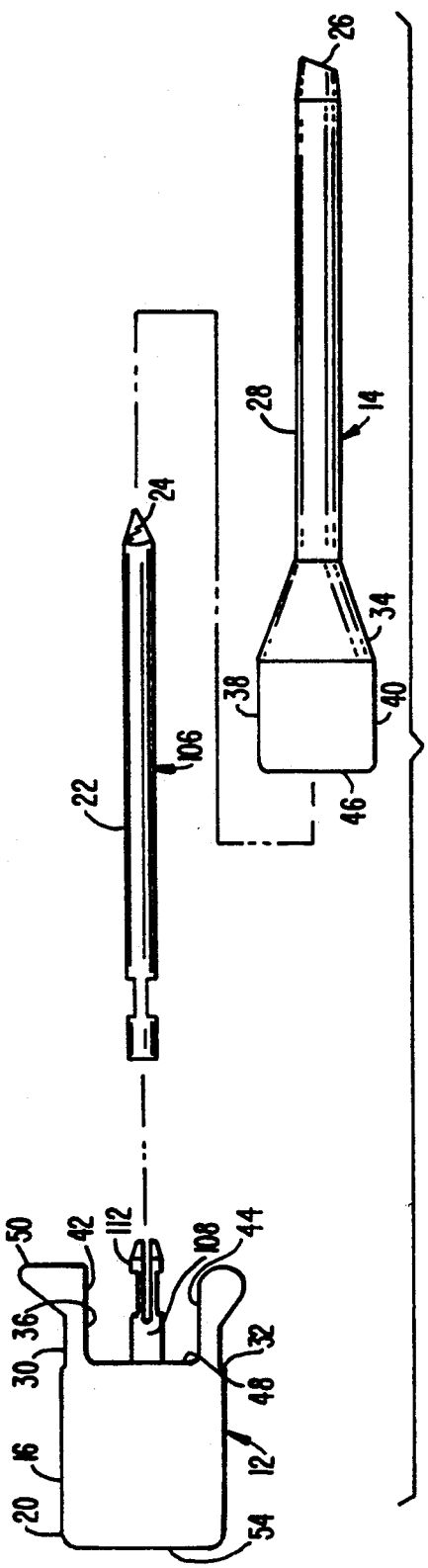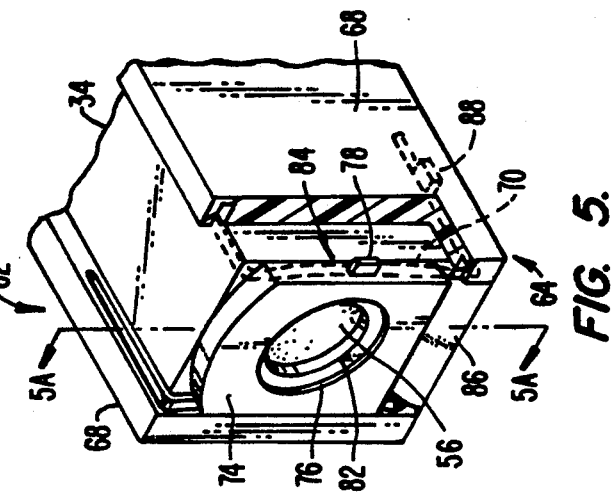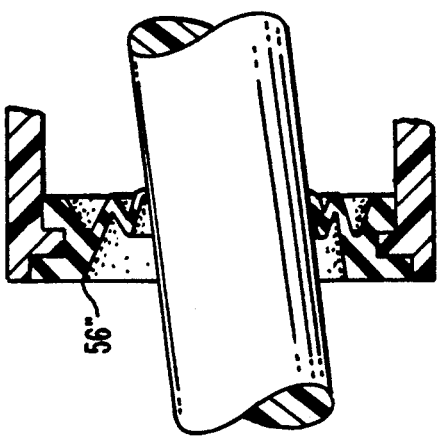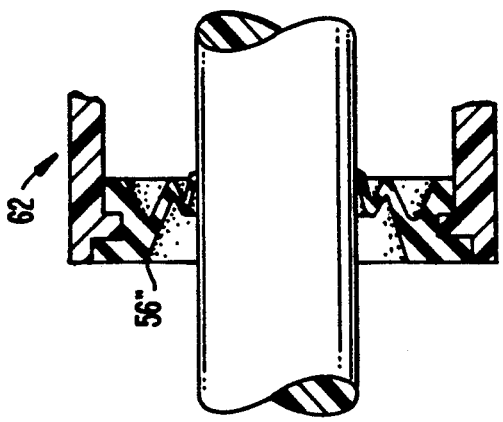

TROCAR WITH MULTIPLE CONVERTERS AND DETACHABLE OBTURATOR

This is a continuation of co-pending application Ser. No. 07/753,326 filed on Aug. 30, 1991, now abandoned.

FIELD OF THE INVENTION

This invention relates to surgical instruments, and particularly to an improved trocar. More specifically, it relates to a trocar for providing communication with a body cavity including converters to adapt to different size surgical tools. It also relates to such a trocar wherein the trocar point and obturator may be detached from the point retraction mechanism. It also relates to a trocar tube body seal design which accepts surgical tool angulation without leakage.

BACKGROUND OF THE INVENTION

Trocars are surgical instruments that have found wide application in many types of operations where puncture-type incisions are to be made. Early configurations were in the form of sharp pointed stylets or obturators closely surrounded by a hollow trocar tube. The sharp point of the stylet normally extends a short distance from the distal end of the trocar tube when the trocar is in its assembled condition. After thrusting through the body wall into a body cavity, the surgeon uses skill to avoid damaging body tissue and body organs. This type of simple trocar is still widely used.

More recently, improved trocars with means for protecting body organs from unintended incidental damage have been devised. Two such improved trocars are shown in U.S. Pat. No. 4,601,710 to Moll and U.S. Pat. No. 4,654,030 to Moll, et al. With these improved devices, the surrounding trocar tube is forced back against a biasing spring by the action of the obturator tip passing through body wall tissue, so as to expose the stylet point. After passing through the body wall, the protective trocar tube returns to its normal position covering the point, thereby protecting against patient organ damage.

While the prior art trocars are very useful, there are some features that are missing, creating problems. One is the lack of versatility in that the forward trocar tube body cannot be used with simple trocar obturators. Another is the lack of adaptability of the trocar tube main seal to various sizes of surgical instruments while maintaining the sealing effect. Still another is the lack of ability to fully accommodate angulation of the surgical instruments while maintaining the sealing effect.

SUMMARY AND OBJECTS OF THE INVENTION

It is to a solution to the above-described and other problems that this invention is directed. The invention provides a detachable distal portion of the obturator including the sharp pointed stylet, which can thus be used as a full featured "point exposed" trocar, or via a single connection, a "point protected" trocar. At the same time, the invention provides a trocar having multiple built-in converters that effectively change the size of the annular seal, which is located on the trocar tube subassembly and which seals around the subsequent surgical tools introduced. In this manner, the same trocar body subassembly and trocar tube subassembly can be used for various sizes of surgical tools. At the same time, the invention provides an improved main body seal which effectively improves converter sealing and resists gas loss due to tool angulation during use.

BRIEF DESCRIPTION OF THE DRAWINGS

FIG. 3 is an exploded view of the device shown in FIG. 1, illustrating the interengagement of its subassemblies;

FIG. 4B is a cross-sectional view showing an alternate embodiment of the seal which accommodates seal angulation of the obturator; FIG. 4C is a cross-sectional view similar to FIG. 4B illustrating how angulation is accommodated;

FIG. 5 is a view similar to FIG. 4 showing a converter subassembly in its operative condition;

DETAILED DESCRIPTION

Figure 1:
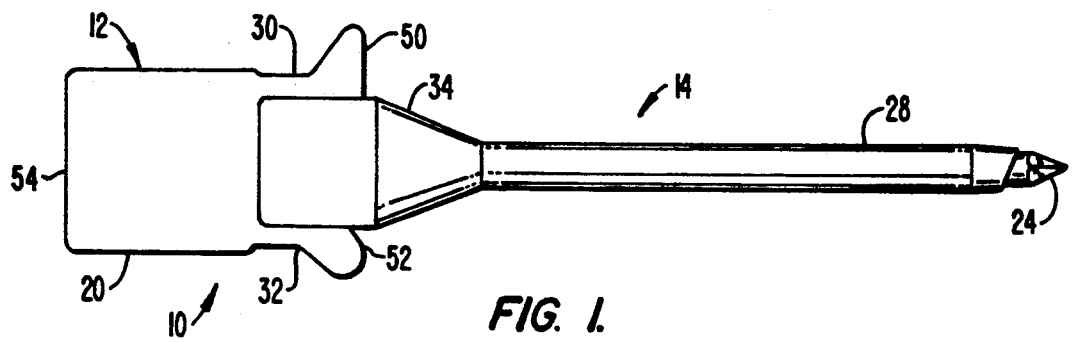
FIG. 1 is a top plan view of the inventive trocar showing its subassemblies fully engaged.
Figure 2:
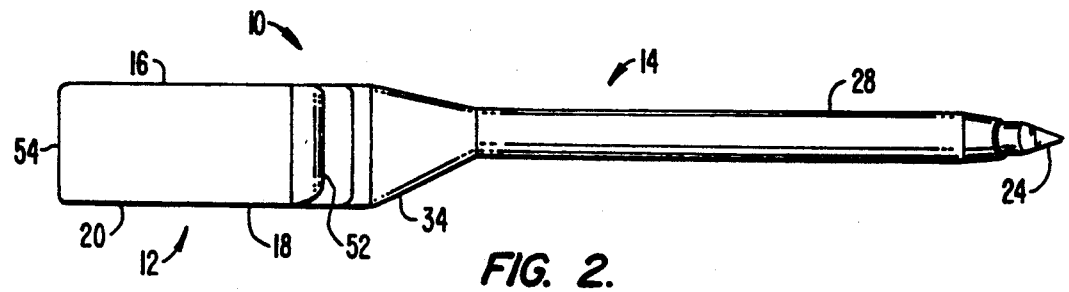
FIG. 2 is a side elevation view of the same.

As shown in FIGS. 1, 2 and 3, trocar 10 is comprised of two interengaging main parts, a trocar body subassembly 12 and a trocar tube subassembly 14. The two subassemblies are designed to be separable from each other. Trocar body subassembly 12 includes upper and lower hollow housings 16, 18, respectively, which combine together to form a grip 20. These housings forming the grip 20 may be made of ABS plastic. Contained within grip 20 is a mechanism (not shown) for extending and retracting the obturator 22 and thereby its attached piercing tip or point 24 within the distal open end 26 of hollow, tapered trocar tube 28. The mechanism for extending and retracting an obturator may be in accordance with that shown in U.S. Pat. No. 4,601,710, aforementioned.

The distal portion of grip 20 is of generally U-shaped configuration defined by a pair of spaced parallel arms 30, 32. Trocar tube subassembly 14 has a body 34, which can also be made of plastic material such as ABS plastic, and is dimensioned to closely fit within slot 36. In the engaged position, parallel side walls 38, 40 of the body 34 closely contact parallel side walls 42, 44 of grip 20. Similarly, rear wall 46 of trocar tube body 34 will be in contact with rear wall 48 of grip 20 within slot 36. In this position, the surgeon can place one finger on each rounded front wall 50, 52, while at the same time holding rear wall 54 in the palm of the hand.

Figure 4:
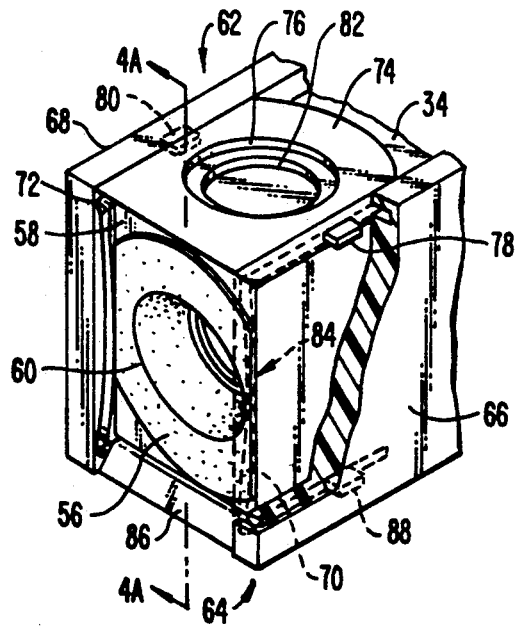
FIG. 4 is an enlarged partial fragmentary top quarter isometric view of the trocar tube subassembly, rotated 90 degrees, illustrating a converter subassembly in its stored condition.
Figure 5A:
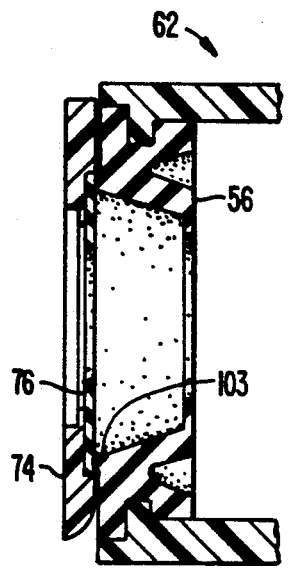
FIG. 5A is a cross-sectional view taken along lines 5A—5A in FIG. 5.

Turning to FIGS. 4 and 5, the inventive converter mechanism will now be described. As with conventional trocars, there is a main seal 56 centrally disposed in an aperture in the rear wall 58 of trocar body 34. This grommet-like seal is of rubber material. The function of the seal in this location is to seal around the obturator (not shown) so as to maintain positive pressure in body 34, so as to prevent the entry of bacteria which might cause infection. The main seal has an aperture 60 therein which closely receives the obturator. Trocar tube subassembly 14 includes therein a flap valve mechanism (not shown) for selectively sealing against main seal 56 so as to selectively close off aperture 60. This flap valve mechanism may also be in accordance with the aforementioned '710 patent disclosure.

Figure 4A:
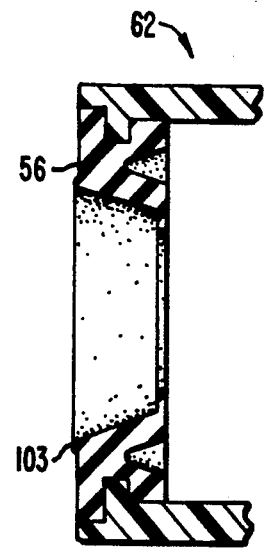
FIG. 4A is a cross-sectional view taken along lines 4A—4A in FIG. 4.

In order to accommodate two different-sized surgical tools, a pair of converters 62, 64 are provided. As may be seen, plate-like top and bottom walls have flange extensions beyond the body 34 to the rear and on both sides. Within the flange extensions, U-shaped grooves or tracks 70, 72 are cut therein. A first sliding door 74 of plastic material having a first alternate seal 76 is normally located as shown on one side of body 34. A pair of pins 78, 80 are captured in the parallel tracks 70, 72 in order to direct the movement of the first door to its operative position shown in FIG. 5. In this position, seal 76 having a smaller aperture 82 than main seal 56 is moved into position over the main seal and thus becomes the operative seal. This permits the use of a smaller surgical tool. It may be noted that tracks 70, 72 make 90 degree bends, and that they are curved at their central point 84 in order to provide a compressive load on the door when it is in its operative position located directly over the main seal. This serves to hold the door 74 in place, as well as to compress first seal 76 against main rib 103 (see FIGS. 4A and 5A). The final location of door 74 is determined by contacting a stop 105 formed by the opposing door 86.

In like manner, a second alternate seal (not shown) mounted on second sliding door 86 and having a pair of pins, one of which is shown at 88, permits the use of a still smaller seal to accommodate a still smaller surgical tool.

As shown in FIGS. 4B and 4C, a still further embodiment of the seal 56" is constructed to be a bellows shape to accommodate angulation of the obturator 106 while still maintaining the sealing effect.

Figure 6:
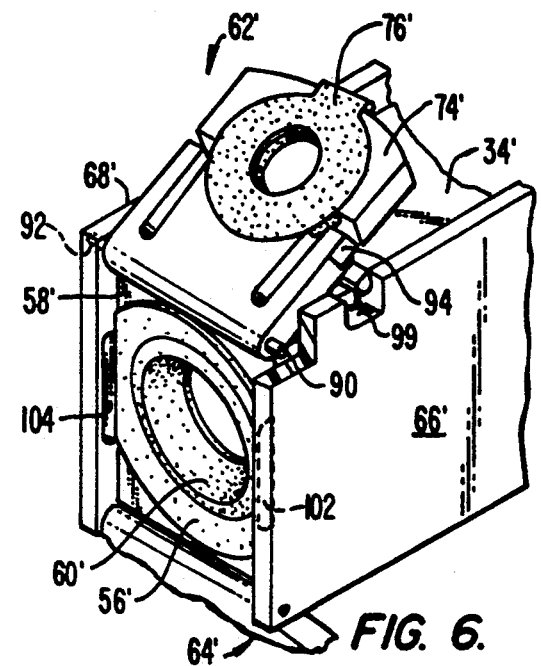
FIG. 6 is a view similar to FIG. 4 of an alternate embodiment of the converter.
Figure 7:
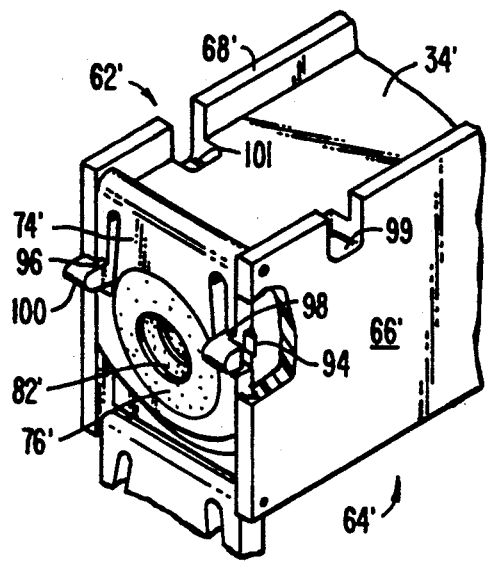
FIG. 7 is a view of the same showing the converter subassembly in its operative condition.

Referring to FIGS. 6 and 7, there is shown an alternate embodiment wherein primes denote elements having their counterparts in the preferred embodiment. With this alternate embodiment, door 74' is hinged rather than on tracks. Hinge pins 90', 92' captured in body 34' serve as pivots to allow door 74' to be articulated from its inoperative position in FIG. 6 to its operative position in FIG. 7. In this position, seal 76' is directly over main seal 56'. Locking of the door 74' in this position is achieved when two ridges 94, 96 on arms 98, 100 snap into grooves 102, 104 on the inner sides of sidewalls 66', 68'. In order to unlock the door, arms 98, 100 are pushed towards each other to remove the ridges from the grooves, and the door may then be returned to its original inoperative position. Recesses 99, 101 are provided to receive arms 98, 100, respectively, when in the inoperative position against the one side of the body 34'. It may be understood that a second door (not shown) with associated locking structure could also be provided so as to permit use of three different sizes of obturators.

Figure 8A:
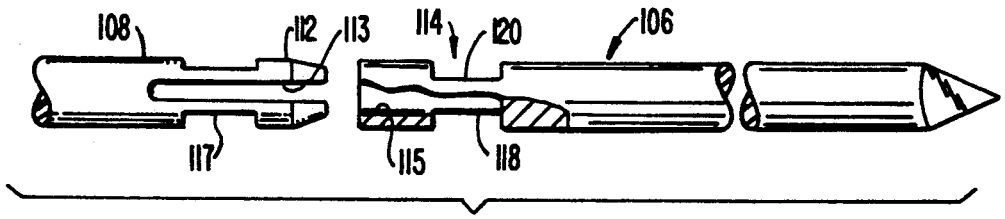
FIGS. 8A and 8B are enlarged partial cross-sectional views of the means for engaging the proximal portion to the distal portion of the obturator.
Figure 8B:
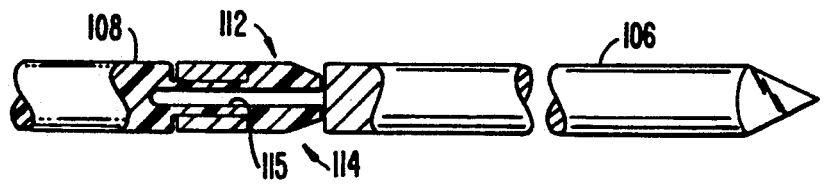

While it is possible to use a different trocar for surgeons using a point exposed trocar (point retracting type shown) subassemblies, each with a different size of obturator, with the converter trocar tube subassemblies thus described, another more economical and versatile approach is possible. As shown in FIGS. 8A and 8B, the obturator may be in two parts, rather than one as is conventional. The distal obturator part 106 is separable from the proximal obturator part 108 by means of a male 112, female 114 snap fitting. Male fitting 112 has an elongated groove 113 therein which facilitates deformation for engagement in bore 115 within female fitting 114. Male fitting 112 also has a groove 117 therearound of a diameter slightly less than that of the inner diameter of bore 115.

Figure 9:
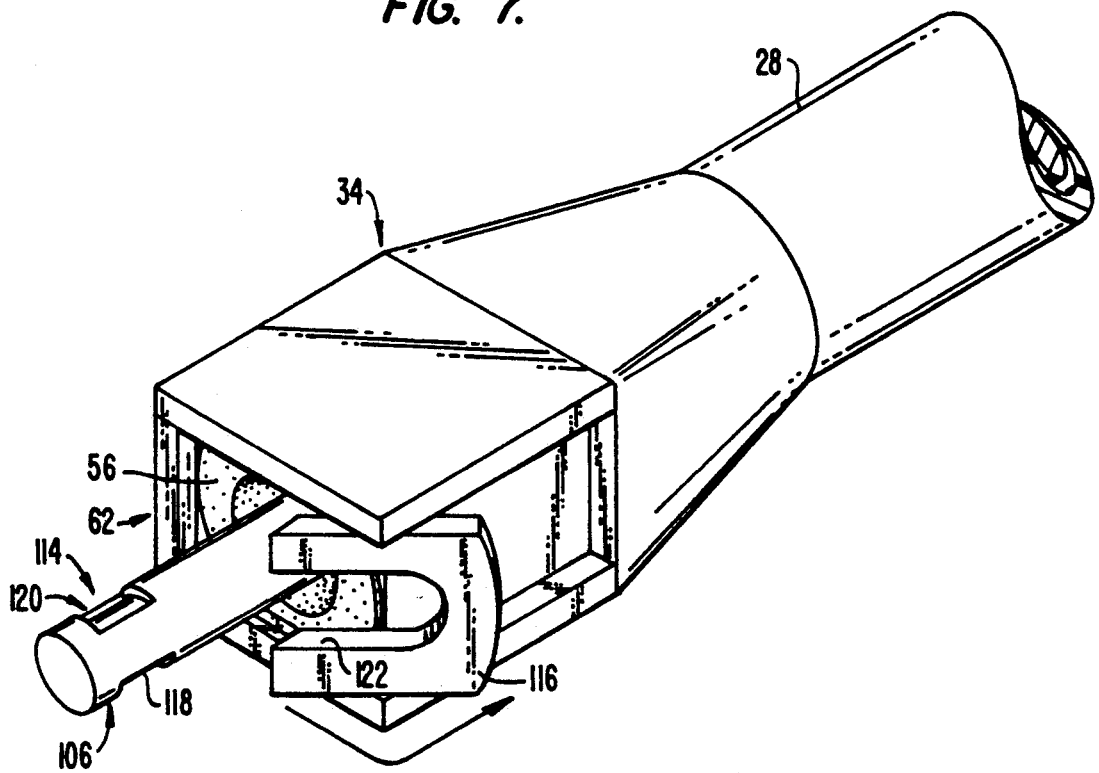
FIG. 9 is an enlarged view of a further alternate embodiment showing a means for retaining the distal obturator portion.

As shown in FIG. 9, it is also possible to use the distal obturator part 106 without the trocar body subassembly 12. In this case, a latch 116 could be configured opposite the converter 62 and operated in a similar manner. That is, the latch occupies the position of a single converter and is movable from a latched position to an unlatched position. The latch 116 has an elongated slot 122 having a width to engage notches 118, 120 in one edge thereof which selectively engages notches 118, 120 of female snap fitting or connector 114, and would be released by movement in the arrow direction. The latch 116 could be configured to slightly lift the distal obturator part 106 for ease of grasping, and prevent the trocar body subassembly from attaching unless the latch were in the down and unattended position.

It is to be understood that while the invention has been described above in conjunction with the preferred specific embodiments, the description and examples are intended to illustrate and not limit the scope of the invention, which is defined by the scope of the appended claims.

What is claimed is:

1. In a trocar having body subassembly including an elongated trocar obturator having a piercing tip at its distal end projecting from said body subassembly, a trocar tube subassembly engaged with said trocar body subassembly, said trocar tube subassembly having a hollow tube defining a distal open end through which said tip may project, and a trocar tube body having a main seal in a proximal end wall thereof, said seal having an aperture therein of a first diameter for admitting a stated largest size surgical tool in sealing relation, wherein the improvement comprises integral converter means, said integral converter means comprising a door member having a first seal having an aperture therein of a different diameter from that of said main seal, and further including means whereby said door member may be positioned from an inoperative position to an operative position over said main seal whereby said trocar tube subassembly may accommodate obturators of different diameters.

2. The invention of claim 1 wherein said converter means comprises at least two converters, each of said converters being dimensioned so as to be of different sizes to accommodate different size surgical tools.

3. The invention of claim 1 wherein said means for positioning comprises tracks in said trocar tube body and pins in said door member, located so as to be movable in said tracks to guide said door member from its inoperative to its operative position.

4. The invention of claim 3 wherein said tracks include a component parallel to said proximal end wall and a component at right angles thereto perpendicular to said end wall and parallel to a side wall of said trocar tube body.

5. The invention of claim 4 wherein said track component parallel to said proximal end wall is curved so that said door member and first seal are compressed against said main seal when said door member is located directly above said main seal.

6. The invention of claim 5 further including a raised rib on said main seal located so as to compress and seal against said first seal when it is in position against said main seal.

7. The invention of claim 5 further including a second door member having a second seal mounted thereon, said second door member including a pair of pins located so as to be movable in said tracks to guide said second door member from an inoperative position to an operative position with said second seal compressed against said main seal.

8. The invention of claim 1 wherein said means for positioning comprises a pair of pins in said door member captured in said trocar tube body so that said door member may be articulated from an inoperative position parallel to a side wall of said trocar tube body to an operative position parallel to said end wall and in contacting relation with said main seal.

9. The invention of claim 8 further including locking means for selectively retaining said door member in its operative position.

10. The invention of claim 8 further including latch means for selectively retaining said obturator fixed with respect to said trocar tube subassembly.

11. The invention of claim 12 wherein said latch means is a latch movable from a latched position engaging said snap connector to an unlatched position not restraining said obturator.

12. The invention of claim 1 wherein said obturator comprises a distal portion including said tip and a proximal portion, and means for connecting said distal and proximal portions.

13. The invention of claim 12 wherein said means for connecting comprises a snap connector.

14. The invention of claim 1 wherein said means for positioning comprises a pair of pins in said member captured in said trocar tube body so that said member may be articulated from an inoperative position parallel to a side wall of said trocar tube body to an operative position parallel to said end wall and in contacting relation with said main seal.

15. The invention of claim 14 further including locking means for selectively retaining said member in its operative position.

16. In a trocar tube subassembly comprising an elongated trocar tube extending from a trocar tube body, an aperture in said body, a main body seal in said aperture adapted to receive and seal against surgical instruments, wherein the improvement comprises said main body seal being of bellows construction so as to accommodate angulation of said surgical tools.

17. The invention of claim 16 wherein said main body seal defines an outer periphery and an aperture disposed therein, wherein said seal is formed into a plurality of pleats intermediate said periphery and said aperture so as to form said bellows construction.

18. The invention of claim 16 wherein said main body seal is made of resilient material.

19. In a trocar having body subassembly including an elongated trocar obturator having a piercing tip at its distal end projecting from said body subassembly, a trocar tube subassembly engaged with said trocar body subassembly, said trocar tube subassembly having a hollow tube defining a distal open end through which said tip may project, and a trocar tube body having a main seal therein, said seal having an aperture therein of a first diameter for admitting a stated larger size surgical tool in sealing relation, wherein the improvement comprises integral converter means, said integral converter means comprising a member having a first seal having an aperture therein of a different diameter from that of said main seal, and further including means whereby said member may be positioned from an inoperative position to an operative position over said main seal, whereby said trocar tube subassembly may accommodate obturators of different diameters.

20. The invention of claim 19 wherein said converter means comprises at least two converters, each of said converters being dimensioned so as to be of different sizes to accommodate different size surgical tools.

21. The invention of claim 19 wherein said means for positioning comprises tracks in said trocar tube body and pins in said member, located so as to be movable in said tracks to guide said member from its inoperative to its operative position.

22. The invention of claim 21, said main seal being in proximal end wall of said body and wherein said tracks include a component parallel to said proximal end wall and a component at right angles thereto perpendicular to said end wall and parallel to a side wall of said trocar tube body.

23. The invention of claim 22 wherein said track component parallel to said proximal end wall is curved so that said first seal is compressed against said main seal when said member is located directly above said main seal.

24. The invention of claim 23 further including a raised rib on said main seal located so as to compress and seal against said first seal when it is in position against said main seal.

25. The invention of claim 23 further including a second member having a second seal mounted thereon, said second member including a pair of pins located so as to be movable in said tracks to guide said second member from an inoperative position to an operative position with said second seal compressed against said main seal.

26. The invention of claim 19 wherein said obturator comprises a distal portion including said tip and a proximal portion, and means for connecting said distal and proximal portions.

27. The invention of claim 26 wherein said means for connecting comprises a snap connector.

28. The invention of claim 27 further including latch means for selectively retaining said obturator fixed with respect to said trocar tube subassembly.

29. The invention of claim 28 wherein said latch means is a latch movable from a latched position engaging said snap connector to an unlatched position not restraining said obturator.

* * * * *